United States Patent [19]

Edge

[11] Patent Number: 5,247,081
[45] Date of Patent: Sep. 21, 1993

[54] PROTECTED BIOTIN DERIVATIVES

[75] Inventor: Michael D. Edge, Congleton, England

[73] Assignee: Imperial Chemical Industries PLC, London, England

[21] Appl. No.: 235,444

[22] Filed: Aug. 23, 1988

[30] Foreign Application Priority Data

Aug. 28, 1987 [GB] United Kingdom ............... 8720394

[51] Int. Cl.$^5$ ...................... C07D 233/40; C07F 9/09
[52] U.S. Cl. .................................. 540/524; 540/542; 544/139; 544/276; 544/277; 546/199; 546/21; 548/113; 536/25.32
[58] Field of Search ............... 544/139, 276, 277, 57; 548/303, 113; 546/199, 21; 540/524, 542

[56] References Cited

U.S. PATENT DOCUMENTS

| | | | |
|---|---|---|---|
| 2,489,237 | 11/1949 | Goldberg | 548/303 |
| 4,876,350 | 10/1989 | McGarrity et al. | 548/303 |
| 4,908,453 | 3/1990 | Cocuzza | 544/57 |

FOREIGN PATENT DOCUMENTS

| | | | |
|---|---|---|---|
| 19788 | 6/1980 | European Pat. Off. | 548/303 |
| 273270 | 7/1980 | European Pat. Off. | 548/303 |
| 119448 | 8/1984 | European Pat. Off. | 548/303 |
| 202758 | 11/1986 | European Pat. Off. | 548/113 |
| 8607363 | 12/1986 | World Int. Prop. O. | 548/303 |

OTHER PUBLICATIONS

Bannwarth, Helvetica Chimica Acts, vol. 68, (7), 1985 pp. 1907–1912.
Ohtsuka, et al Nucleic Acid Res. 10(21) 1982 pp. 6553–6570.
Sinha et al Nucleic Acid Res. 12(11) 1984 pp. 4539–4557.
Fourney, et al. Tetrahetron Letters 25(40) 1984 pp. 4511–4515.
Nippon Soda, Chemical Abstracts vol. 83 1975, Abstract 28226v.
Chimia. 41(5), 1987 pp. 148–150.

*Primary Examiner*—Mukund J. Shah
*Assistant Examiner*—E. C. Ward
*Attorney, Agent, or Firm*—Cushman, Darby & Cushman

[57] ABSTRACT

Processes for the preparation of biotinylated polynucleotides and analogues thereof and protected intermediate products for use in such processes are described and claimed. The processes may be conveniently used in the automated synthesis of biotinylated polynucleotide on a DNA synthesizer. The polynucleotides so prepared may be used as labelled probes e.g. as diagnostic tools for clinical and research uses.

8 Claims, No Drawings

PROTECTED BIOTIN DERIVATIVES

The present invention relates to processes for the preparation of biotinylated polynucleotides and analogues thereof and to intermediates for use in such processes.

The use of labelled polynucleotide probes is well known for a wide range of applications as described in, for example, Lewin, Science 221:1167 (1983) and Klausner et al, Bio/Technology, 1: 471 (1983). Labelled oligonucleotide probes are of particular interest as diagnostic tools for clinical and research uses.

Conventional radiolabelled probes are efficient and sensitive, but are associated with several problems which mitigate against routine use for screening for example in clinical laboratories. Thus radiolabelled probes are potentially hazardous and pose problems of disposal. Furthermore radiolabelled probes are often unstable and have a limited shelf-life as a result of the relatively short half life of the radioactive materials used as labels, especially $^{32}P$. Moreover autoradiographic detection can be time consuming and the handling of radiolabelled probes requires personnel with the appropriate safety training.

There is therefore a desire to use non-radioactive methods of labelling probes and certain such methods have been described in the literature for example D. C. Ward at the 1981 ICN-UCLA Symposium held in Keystone, Colo. on Mar. 15–20, and published in "Developmental Biology Using Purified Genes", 1981 XXIII, 1981 pages 647–658, Academic Press, Editor Donald D Brown et al; and A. D. B. Malcolm et al. Abstracts of the 604th Biochemical Society Meeting, Cambridge, England (meeting of 1 Jul. 1983). Probes labelled with biotin have also been widely described in the literature.

Biotin is of particular interest in the labelling of oligonucleotides since it is capable of forming a strong interaction with avidin thereby enabling for example enzymatically-activated signalling systems or enzyme labels to be conveniently attached to an oligonucleotide hybridisation probe.

Methods for the attachment of a biotin residue to oligonucleotides via a phosphate link are known and have for example been described in our European Patent Publication No. 202758. Such methods involve phosphotriester chemistry which inter alia is incompatible with phosphoramidite chemistry which may be used in the automated synthesis of nucleotide sequences for example in a DNA synthesiser. Moreover, no convenient method has, hitherto, been described of linking biotin in protected form to a nucleotide sequence using phosphoramidite chemistry.

The present invention is based on the discovery of processes which at least in part obviate the above-mentioned difficulties and on intermediates therefor.

Thus according to one feature of the present invention there is provided a process for the preparation of a compound of formula Ia as set out hereinafter [in which m is 4 or 5, X represents a direct link, —O—P(O)(OR$^6_a$)—O—, —S—, —O—, —CONH—, —NHCONH— or N—R$^8$ (wherein R$^8$ represents a straight chain or branched $C_{1-10}$ alkyl group), p is an integer from 0 to 16 with the proviso that where X is other than a direct link p is an integer of at least 2, R$^6_a$ represents a hydrogen atom or a phosphate protecting group and Z' represents a nucleotide sequence in unprotected form or in a form in which base and/or phosphate moieties carry protecting group(s), and the nucleotide sequence is optionally bound to a support] or an isoequivalent thereof, which process comprises deprotecting a compound of formula II as set out hereinafter [in which m, p, X, R$^6_a$ and Z' are as hereinbefore defined and J and K which may be the same or different, each represents a hydrogen atom or a protecting group compatible with nucleotide phosphorylation which group increases the lipophilicity of the compound, at least one of J and K being other than hydrogen] or an isoequivalent thereof; whereby to remove any J or K group being other than hydrogen to obtain a compound of formula Ia or isoequivalent thereof.

The term "isoequivalent" as used herein, generally means a compound which serves the same function as the compound of the formula to which the term refers and which is capable of forming a complex with a biotin binding moiety such as avidin, streptavidin or an anti-biotin antibody in the absence of any J or K group being other than hydrogen. The "isoequivalent" will thus generally be linked or be capable of linkage to a nucleotide sequence via a phosphate or phosphite group and will generally carry or be capable of carrying at least one protecting group compatible with nucleotide phosphorylation and which increases the lipophilicty of the compound over a corresponding compound in which no such protecting group is present.

The conditions under which the deprotection is effected will necessarily be dependent on the nature of the protecting groups J and/or K. Thus for example acid labile protecting groups may be removed in the presence of one or more aqueous acids, for example an organic acid such as an acetic acid or a mineral acid such as hydrochloric acid, whilst base labile protecting groups may be removed in the presence of one or more bases such as an aqueous base, for example ammonium hydroxide.

A compound of formula II is preferably used in which J and/or K represents tetrahydropyranyl e.g. tetrahydropyran-2-yl, 6-methoxy-tetrahydropyranyl e.g. 6-methoxy-tetrahydropyran-2-yl, furyl e.g. 2-furyl, dimethoxytrityl e.g. 4,4'-dimethoxytrityl, xanthenyl e.g. 9-phenylxanthenyl, tetrahydrothiopyranyl e.g. tetrahydrothiopyran-2-yl, 4-methoxytetrahydrothiopyranyl e.g. 4-methoxytetrahydrothiopyran-2-yl, benzoyl, or an acyl group e.g. of up to 6 carbon atoms e.g. 3-6 carbon atoms. Preferred protecting groups are tetrahydropyran-2-yl, 6-methoxy- tetrahydropyran-2-yl, or dimethoxytrityl groups. A compound of formula II in which at least one of J and K is dimethoxytrityl may be advantageous since a colour change is obtained on its removal. When J and/or K represents a dimethoxytrityl group this may be conveniently removed by treatment with an aqueous acid, for example aqueous trifluoroacetic acid or aqueous acetic acid, preferably aqueous acetic acid, or an aqueous mineral acid such as aqueous hydrochloric acid. When J and/or K represents a tetrahydropyranyl group this may be conveniently removed by treatment with an aqueous acid such as an aqueous mineral acid for example aqueous hydrochloric acid.

Conveniently only one of J and K represents a protecting group, the other of J and K representing hydrogen.

A compound of formula II is advantageously used in which X is other than the group of formula N—R$^8$ as hereinbefore defined. Normally when X is —CONH— or —NHCONH— then m is 4. X is preferably a direct link or the group —O—P(O)(OR$^6_a$)—O—. Thus for example a compound of formula II may be used in which X is a direct link, m is 5 and p is 0 or even in which X is —O—P(O)(OR$^6_a$)—O—, m is 5 and p is 8.

Where a compound of formula II is used in which R$^6_a$ represents a phosphate protecting group (R$^6$ as referred to hereinafter) that group will generally be capable of serving both as a phosphate protecting and as a phosphite protecting group. Such groups include for example a methyl, 2-cyanoethyl, 2-chlorophenyl, 2,2,2-trihalo-1,1-dimethyl-ethyl, 5-chloroquinolin-8-yl, 2-methylthioethyl group or a 2-phenylthioethyl group in which the phenyl ring may optionally carry a substituent selected from for example halogen, e.g. chlorine, or NO$_2$. Commonly R$^6$ will represent a methyl or a 2-cyanoethyl.

Where a compound of the formula II in which R$^6_a$ is a hydrogen atom is desired then the phosphate protecting group may be removed using methods known per se, for example using the methods outlined in the above preparations of compounds of the formula I.

Z' in the compound of formula II or Ia may be unprotected or in protected form. It will be appreciated that the length of the nucleotide sequence comprised by Z' is only limited by the length of the sequence which may be constructed e.g. on a DNA synthesiser. Polynucleotide sequences of up to 150 nucleotides, for example up to 100 nucleotides may be prepared. Commonly Z' represents an oligonucleotide sequence of, for example, 6 to 30 nucleotide units, conveniently 12 to 25 nucleotide units. Where it is intended that the oligonucleotide sequence be used for the detection of e.g. genetic disorders the oligonucleotide sequence is preferably of 17 to 20 nucleotide units. The present invention may thus, for example, be of interest in the production of oligonucleotide primers for use in the PCR (polymerase chain reaction) technique described in U.S. Pat. Nos. 4,683,195 and 4,683,202.

Where the nucleotide sequence is in protected form each nucleotide unit may carry a phosphate protecting group for the phosphate groups of the sugar-phosphate backbone of the nucleotide sequence, such protecting groups being well documented in the literature. (N. D. Sinha et al, Nucleic Acids Research (1984), 12, p4539, J. L. Fourrey and J. Varenne, Tetrahedron Letters (1984) 25, 4511-4514 or E. Ohtsuka et al, Nucleic Acids Research, 1982, 10, 6553-6570). Moreover appropriate phosphate protecting groups are apparent to nucleotide chemists and may for example include the phosphate protecting groups described above in relation to R$^6$, for example methyl or 2-cyanoethyl. Furthermore the nucleotide sequence which may include any of the conventional nucleosides (deoxy)cytidine, (deoxy)adenosine, (deoxy)guanosine and either thymidine or (deoxy)uridine as well as base modified nucleosides capable of base pairing with one of the conventional nucleosides referred to above. Such base modified nucleosides include (deoxy)inosine and (deoxy)8-azaguanosine. Where appropriate the base portion of a nucleotide present in the nucleotide sequence may carry a protecting group. Thus for example the amine substituent in adenine, cytosine and guanine may carry any convenient protecting group, such protecting groups being well documented in the literature (for example, E. Ohtsuka et al, Nucleic Acids Research (1982), 10, 6553-6570).

Moreover appropriate base protecting groups are apparent to nucleotide chemists and include particularly isobutyryl and benzoyl, the isobutyryl group being particularly appropriate as a protecting group for guanine and the benzoyl group being particularly appropriate as a protecting group for cytosine and adenine. Protected bases may thus include for example N$^4$-benzoylcytosine, N$^6$-benzoyladenine and N$^2$-isobutyryl guanine. It will be appreciated that not all bases will require protection, thus for example thymine and uracil may not require protecting groups.

The above-mentioned phosphate protecting groups, nucleotide phosphate protecting groups and base protecting groups may all be removed according to techniques well documented in the literature. Such deprotection methods are apparent to nucleotide chemists.

Where the phosphate protecting group contains a sulphide linkage this linkage will conveniently be oxidised to the corresponding sulfoxide or sulphone before removal.

As outlined for the protecting groups J and K above the conditions under which the deprotection is effected will necessarily be dependent on the nature of the phosphate, nucleotide phosphate and base protecting groups.

By way of example, where the phosphate and/or nucleotide phosphate protecting group is a methyl group, this may conveniently be removed by treatment with a nucleophilic agent such as a phenolate ion, preferably a thiophenolate ion or a base such as ammonium hydroxide; where the above mentioned protecting group is a 2-cyanoethyl group this may be removed by treatment with a base, as exemplified above.

The nucleotide sequence may if desired be bound to a support, for example a solid support such as a controlled pore glass support. Techniques for cleaving the nucleotide sequence from the support are well documented in the literature and indeed nucleotide-support cleaving techniques are apparent to nucleotide chemists. It can be seen that where the conditions chosen for the above mentioned cleavage and deprotection are identical or similar then these operations may proceed simultaneously.

Where deprotection of the compound of formula II results in the production of a compound of formula Ia which is not a compound of formula I any protecting groups present may, if desired, be removed for example by methods known per se and/or where the compound of formula Ia is bound to a support, said compound may, if desired, be cleaved from the support for example by methods known per se; whereby a compound of formula I is obtained.

It will be appreciated that the removal of the protecting groups and the cleavage of the compound of formula II or Ia from the support may be effected in any convenient order and this may be dependent on the individual reactions conditions selected in any particular case.

Thus for example (a) a fully protected compound of formula II, bound to a support may be subjected to a reaction which removes the phosphate protecting groups and cleaves the nucleotide sequence from the support, the compound thus obtained may then be subjected to a further deprotection step in which the base protecting groups are removed and finally the compound thus obtained may be subjected to a deprotection step in which the protecting group(s) J and/or K is (are) removed to yield a compound of formula I.

Alternatively (b) a fully protected compound of formula II, bound to a support may be subjected to a deprotection step in which the protecting group(s) J and- /or K is (are) removed, the compound thus obtained is then subjected to a reaction which removes the phosphate protecting groups and cleaves the nucleotide sequence from the support and finally the compound thus obtained is subjected to a further deprotection step in which the base protecting groups are removed to form a compound of formula I.

Alternatively for example (c) a fully protected compound of formula II, bound to a support, may be subjected to a deprotection step in which the phosphate protecting groups are removed, the compound thus obtained is then subjected to a cleavage reaction in which the nucleotide is cleaved from its support, the compound thus obtained is then subjected to a deprotection step in which the base protecting groups are removed and finally the compound thus obtained is subjected to a deprotection step in which the protecting group(s) J and/or K is (are) removed to yield a compound of formula I.

Alternatively for example (d) a fully protected compound of formula II, bound to a support, may be subjected to a reaction which removes the phosphate protecting groups and cleaves the nucleotide sequence from the support, the compound thus obtained being subjected to a deprotection step in which the protecting group(s) J and/or K is (are) removed and finally the compound thus obtained is subjected to a deprotection step in which the base protecting groups are removed to yield a compound of formula I.

Alternatively for example (e) a fully protected compound of formula II, bound to a support, may be subjected to a deprotection step in which the protecting group(s) J and/or K is (are) removed, the compound thus obtained then subjected to a further deprotection step in which the phosphate protecting groups are removed, the compound thus obtained then subjected to a cleavage reaction in which the nucleotide sequence is cleaved form the support and finally the compound obtained subjected to a deprotection step in which the base protecting groups are removed to yield a compound of formula I.

Alternatively, for example, (f) a fully protected compound of formula II, bound to a support, may be subjected to a deprotection step in which the phosphate protecting groups are removed, the compound thus obtained is then subjected to a reaction which removes the base protecting groups and cleaves the nucleotide sequence from its support and finally the compound thus obtained is subjected to a deprotection step in which the protecting group(s) J and/or K is (are) removed to yield a compound of formula I.

Alternatively, for example, (g) a fully protected compound of formula II, bound to a support, may be subjected to a deprotection step in which the protecting group(s) J and/or K is (are) removed and the compound thus obtained subjected to a reaction which cleaves the nucleotide sequence from the support and removes the phosphate and base protecting groups.

A particular sequence for the removal of the protecting groups and the cleavage of the compound of formula II or Ia from the support is sequence (a) as outlined above.

According to another and independent feature of the present invention there is provided a process for the preparation of a compound of the formula II as defined above or an isoequivalent thereof, which process comprises oxidising a corresponding compound of the formula III as set out hereinafter [wherein m, p, J, K, Z', X and $R^6{}_a$ are as hereinbefore defined] or an isoequivalent thereof.

Phosphite oxidising agents for use in the above mentioned oxidation are known to the skilled man, and may conveniently be selected from bleaches; peracids, such as perbenzoic acids, hypochlorites e.g. sodium hypochlorite, permanganates e.g. potassium permanganate; peroxides, such as bis(trimethysilyl)peroxide; or iodine, preferably aqueous iodine.

According to another and independent aspect of the present invention we provide a process for the preparation of a compound of the general formula III [as hereinbefore defined] or an isoequivalent thereof wherein said process comprises coupling a compound of the formula IV as set out hereinafter (wherein J, K, m, p, X, are as defined above, $R^4$ and $R^5$, which may be the same or different, each represent a 1-10C straight chain or branched alkyl group, preferably methyl or isopropyl, or $R^4$ and $R^5$ together with the nitrogen atom therebetween represent a 5-7 membered heterocyclic ring containing 1,2,3 or 4-heteroatoms, any heteroatom present in addition to nitrogen being selected from oxygen, nitrogen and sulphur, and $R^6$ corresponds to $R^6{}_a$ as hereinbefore defined, but is other than hydrogen); or an isoequivalent thereof with a nucleotide sequence of the formula Z" which corresponds to a nucleotide sequence of the formula Z' as defined above but wherein the point of attachment to the compound of formula IV is unprotected such as to allow coupling at that point, whereby to obtain a compound of formula III as hereinbefore defined or an isoequivalent thereof. Where a compound of formula III in which $R^6{}_a$ is a hydrogen atom is desired then the phosphate protecting group may be removed using methods known per se.

Where a compound of formula IV is used in which $R^4$ and $R^5$ together with the nitrogen atom therebetween represent a heterocyclic ring, the ring may be saturated or less preferably unsaturated and conveniently has 5 or 6 ring members, for example 6 ring members. The heterocyclic ring will conveniently contain no more than 2 heteroatoms, such rings being exemplified by piperidino and morpholino groups, preferably a morpholino group, for example the 4-morpholino group.

The skilled nucleotide chemist will select suitable conditions for binding the nucleotide sequence to the support and releasing it therefrom and also for the above mentioned coupling. A convenient point for attachment of the compound of formula IV is the 5' end of the oligonucleotide sequence. Conveniently the nucleotide sequence is bound to the support prior to the coupling reaction. The coupling reaction is advantageously performed in apparatus for the automated synthesis of nucleotides, such as a DNA synthesiser. The coupling may for example be repeated such as once or twice. The coupling may optionally be performed in the presence of one or more organic solvents, for example polar solvents such as dichloroethane or acetonitrile or a mixture thereof.

According to another and independent aspect of the present invention we provide a process for the preparation of a compound of the general formula IV [as defined above] or an isoequivalent thereof which process comprises reacting a compound of the general formula VI (as set out hereinafter) [wherein J, K, m, p and X are as defined above but $R^6{}_a$ does not represent hydrogen] or an isoequivalent thereof, with a compound of the general formula V (as set out hereinafter) wherein $R^4$, $R^5$ and $R^6$ are as defined above, and L is a displaceable group whereby to form a compound of formula IV as hereinbefore defined or an isoequivalent thereof.

A compound of formula V is conveniently used in which L is a halogen atom particularly a chlorine or bromine atom, more particularly a chlorine atom. Suitable reaction conditions will be apparent to the skilled man. The reaction is conveniently performed in the presence of one or more solvents such as an aprotic solvent such as an ether, or haloalkane such as methylene chloride or carbon tetrachloride, but more particularly a dihalomethane solvent such as dichloromethane.

According to another and independent aspect of the present invention we provide a process for the preparation of a compound of the general formula VI [wherein X represents a direct link and J, K, m and p are as defined above] or an isoequivalent thereof which process comprises reducing a corresponding compound of the general formula VII as set out hereinafter [wherein J, K, m and p are as defined above, and R represents a group reduceable to the corresponding alcohol] or an isoequivalent thereof, whereby to form a compound of formula VI as hereinbefore defined or an isoequivalent thereof. The reduction is conveniently performed in the presence of a reducing agent. Appropriate reducing agents will be apparent to the skilled man and include for example a complex metal hydride such as lithium aluminium hydride; or diborane, conveniently lithium aluminium hydride (H. C. Brown and S. Krishnamurphy, Tetrahedron (1979), 35, p567-607). The reduction may optionally be carried out in the presence of one or more solvents such as organic solvents for example an aprotic solvent, in particular tetrahydrofuran (THF). A compound of formula VII is conveniently used in which R represents inter alia a carboxylic acid anhydride, imidazolide or ester thereof such as an aliphatic ester, in particular an alkyl ester such as a C1-6 alkyl ester, e.g. methyl, ethyl, propyl, butyl, pentyl, and hexyl esters, preferably a methyl ester.

According to another and independent aspect of the present invention we provide a process for the preparation of a compound of the general formula VI [wherein X represents —O—P(O)(OR$^6_a$)—O— and J, K, m, p and R$^6_a$ are as defined above] or an isoequivalent thereof which process comprises reacting a phosphorylated biotinol derivative of the general formula XIX [wherein J, K, m and R$^6_a$ are as defined above] or an isoequivalent thereof with an appropriate diol of the general formula IX [wherein n is as defined above], whereby to form a compound of formula VI or an isoequivalent thereof as hereinbefore defined.

A compound of formula XIX or an isoequivalent thereof may be obtained by reacting a compound of the general formula VIII (wherein J, K and m are as defined above) or an isoequivalent thereof with a phosphorylating agent. It will be appreciated that the selection of a convenient phosphorylating agent will enable compounds of formula XIX wherein R$^6_a$ represents a phosphate protecting group R$^6$ (as defined hereinbefore) to be prepared. Convenient phosphorylating agents will be apparent to the skilled man and include phosphoryl chloride and (substituted)aryl phosphorodi(1,2,4-triazolide)s such as for example 2-chlorophenyl phosphorodi(1,2,4-triazolide) generated e.g. from the reaction of 1,2,4-triazole and 2-chlorophenyl phosphorodichloridate in the presence of a base such as pyridine. Phosphorylation may be effected in the presence of a mixture of one or more organic solvents such as an aprotic solvent, for example pyridine and the like. A compound of formula VI wherein R$^6_a$ represents hydrogen may be selectively protected using methods known per se to give a corresponding compound wherein R$^6_a$ represents a phosphate protecting group $R^6$ as hereinbefore defined.

According to another and independent aspect of the present invention we provide a process for the preparation of a compound of the general formula VI [wherein X represents —S—, —O—, or N—R$^8$ and J, K, m, R$^8$ and p are as defined above] or an isoequivalent thereof, which process comprises reacting a compound of the general formula X [wherein J, K and m are as defined above and L' represents a displaceable group] or an isoequivalent thereof with compound of the general formula XI [wherein p is as defined above and Q represents the anion of a hydroxy group, a thiol group or an amine group of the formula N—R$^8$ (wherein R$^8$ is as defined above) whereby to form a compound of formula VI or an isoequivalent thereof as defined above.

Convenient displaceable groups of the formula L' will be apparent to the skilled man and include halogen atoms, such as chlorine or bromine, mesylate and tosylate groups, conveniently a tosylate group. The rection may be effected in the presence of a mixture of one or more organic solvents, such as an aprotic solvent, for example dimethylformamide (DMF) and the like. Compounds of the general formula X may be prepared from the corresponding biotinol derivatives of formula VIII using methods known per se. By way of example, where a compound of formula X having a tosylate group as the displaceable group L' is desired this may be conveniently prepared by the reaction of the corresponding alcohol of the formula VIII with a tosyl halide, such as tosyl chloride.

According to another and independent aspect of the invention we provide a process for the preparation of a compound of the general formula VI [wherein J, K, m and p are as defined above and X represents —CONH—] or an isoequivalent thereof which process comprises reacting a compound of the general formula XII [wherein J, K and m are as defined above and R' represents a carboxylic acid group or a derivative thereof] or an isoequivalent thereof with a hydroxyalkylamine of the formula XIII [wherein p is as defined above] whereby to form a compound of formula VI or an isoequivalent thereof as defined above. Convenient carboxylic acid derivatives include esters, such as aliphatic esters, for example $C_1$–$C_6$ alkyl esters; anhydrides and acid chlorides. Convenient reaction conditions will be apparent to the skilled man.

According to a further and independent aspect of the present invention we provide a process for the preparation of a compound of the general formula VI [wherein J, K, m and p are as defined above and X represents —NHCONH—] or an isoequivalent thereof which process comprises reacting a compound of the general formula XVII [wherein J, K and m are as defined above] or an isoequivalent thereof with a compound of the general formula XVIII [wherein p is as defined above and W represents a displaceable group] whereby to form a compound of the formula VI or an isoequivalent thereof. Convenient displaceable groups will be apparent to the skilled man and include aryloxy groups such as phenyloxy.

Compounds of the general formula XVII may be obtained from compounds of the formula XII as defined above using methods known per se, for example using methods based on the Curtius rearrangement. Compounds of the general formula XVIII may be obtained from corresponding amines of the formula XIII (wherein p is as defined hereinbefore) using methods known per se.

According to a further and independent aspect of the present invention we provide a process for the preparation of a compound of the general formula VII, VIII or XII [wherein J, K, m, p, R and R' are as hereinbefore defined] or an isoequivalent thereof which process comprises reacting a corresponding derivative of the general formula XIV, XV or XVI [wherein J, K, m, p, R and R' are as defined above] or an isoequivalent thereof with a group of the formula J' and/or with a group of the formula K' [wherein the compounds J' and K' are precursors of the moieties J and K respectively as defined above] whereby to form a compound of formula VII, VIII or XII or an isoequivalent thereof as defined above. Convenient reaction conditions will be apparent to the skilled man. The expression "precursors" is used herein to indicate compounds selected such that reaction thereof with a compound of the formula VIII as defined above results in the introduction of the desired group(s) J and/or K. to give the corresponding compound of formula VII. Thus in particular when the chosen group J and/or K is a tetrahydropyran group e.g. tetrahydropyran-2-yl or 6-methoxytetrahydropyran-2-yl, convenient precursors therefor are 2,3-dihydropyran and 2-methoxy-2,3-dihydropyran respectively. When the chosen group J and/or K is a dimethoxytrityl group, a convenient precursor therefor is dimethoxytrityl chloride or dimethoxytrityl bromide.

Compounds of the general formula VIII are known in the art, see e.g. European patent application no. 86302750.4 (Publication No. 202,758) or may be prepared using methods known per se from known biotin derivatives.

The compounds of the general formulae IV, III and II as defined above are novel and each of the aforementioned general formulae represents a further and independent aspect of the present invention. Compounds of formula VI are also believed to be novel and constitute a further feature of the present invention. Such compounds of formula VI will include compounds in which neither J nor K may represent $C_{1-3}$ alkyl, $C_{1-3}$ alkenyl, acetyl, methoxycarbonyl, phenyl, benzyl or benzoyl.

Compounds of formula VII in which neither J nor K may represent $C_{1-3}$ alkyl, $C_{1-3}$ alkenyl, acetyl, methoxycarbonyl, phenyl, benzyl or benzoyl constitute a further feature of the present invention.

Particular groups of compounds include those of the above formulae wherein X is a direct link, or where m is 5, or where p is 0, or where X is —O—P(O)(OH-)—O—, or p is 8. More particular groups of compounds include those of the above formulae wherein X is a direct link, m is 5, and p is 0 or wherein X is —O—P(O)-(OH)—O— and p is 8.

The present invention also relates to a process which comprises two or more of the above-defined processes in sequence. Conveniently any one or more of the said above-defined processes may be effected in a DNA synthesiser and thus according to a further feature of the present invention we provide a DNA synthesiser programmed to effect at least one of the processes hereinbefore defined. With the exception of the removal of base protecting groups the processes for the preparation of the compounds of formulae I, Ia, II and/or III are particularly appropriate for use in a DNA synthesiser.

The biotinylated oligonucleotide sequences prepared by the present invention may conveniently be used as probes, for example to detect complementary sequences e.g. in hybridisation assays, in a similiar manner to those derivatives prepared by methods known in the art. Convenient probes which may be prepared according to the invention are disclosed in European Patent Application, publication number 202,758.

The invention is illustrated, but not limited by the following Examples in which the oligonucleotide sequence interferon alpha$_2$ 55 is as follows:

AAGAAATACAGCCCG

The letters A to M appearing in parentheses in the Examples refer to the figures in the specification immediately after the Examples.

The constitution of various reagents in the example is as follows:

| | |
|---|---|
| PBS - 150 mM NaCl + 10 mM sodium phosphate at pH 7.4 | |
| SSC - 0.15M NaCl + 0.015M sodium citrate | |
| Denhardt's reagent | 0.02% BSA |
| | 0.02% Ficol 400,000 |
| | 0.02% PVP |

The following contractions are used:

DMF - dimethylformamide
DNA - deoxyribonucleic acid
PBS - phosphate buffered saline
SDS - sodium dodecyl sulphate
BSA - bovin serum albumin
PVP - Polyvinyl pyrrolidene
HEPES - (N-2-hydroxyethyl-N$^1$-2-ethane sulphonic acid)
TRIS - tris(hydrrymethyl)aminomethane
NBT - nitro blue tetrazoleum
BCIP - 5-bromo-4 chloro-3-indolylphosphate The following are trade marks:

| | | |
|---|---|---|
| Fractosil | Partisil 10-SAX | Ficol 400,00 |
| Triton-X-100 | Core Buffer | Nonidet P40 |
| Tween | C18-μ Bondapak | |

Example 1

Biotinolyl hydroxy [5'-(interferon-alpha$_2$-55)]phosphine oxide (A)

Hydrochloric acid (0.1N, 600 μl) was added to hydroxy [5'-(interferon-alpha$_2$-55)] N$^1$-(tetrahydro-2-pyranyl)biotinolyl phosphine oxide (B) 0.1 μmol obtained as described below and the mixture allowed to stand for 45 minutes at 22° C. Ammonium hydroxide (sp.gr 0.91, 126 μl) was added and the biotinylated oligonucleotide derivative (A) was then purified by a two stage High Pressure Liquid Chromatography (HPLC) procedure (as described by C. R. Newton et al, Anal. Biochem, 1983, 129, p22-30).

The first HPLC on Partisil 10-SAX ion exchange resin (using buffer system VI) gave the biotinylated oligonucelotide (A) as the most retained peak with a retention time of 29.8 minutes. The biotinylated oligonucleotide derivative (B) had a retention time of 28.9 minutes and the parent oligonucleotide sequence interferon-alpha$_2$-55 (C) had a retention time of 28.6 minutes, when analysed under idential conditions.

The second HPLC on μ-Bondapak C-18 (10–45% in 40') give (A) with a retention time of 20.0 minutes, (B) and (C) had retention times of 24.0 and 18 minutes respectively when analysed under identical conditions.

The protected biotinylated oligonucleotide (B) used as starting material was prepared as follows:

a) N$^1$-(Tetrahydropyran-2-yl)biotin methyl ester.

Toluene-4 sulphonic acid monohydrate (11.4g) was added to a stirred solution of freshly distilled 2,3-dihydro-4H-pyran (10.2 g) and D(+) biotin methyl ester (3 g) [E. A. Bayer and M. Wilcheke, Methods of Biochemical Analysis, 26, page 1] in dichloromethane (40ml) at 0° C. The mixture was stirred for 10 minutes at this temperature and then at 22° C. for 1.5 hours. The solution was washed successively with water (50 ml), saturated sodium bicarbonate solution (50 ml) and saturated brine solution (50 ml) then dried over anhydrous magnesium sulphate and evaporated. The residue was taken up in the minimum quantity of diethyl ether and triturated with petroleum ether (b.p.40°-60° C.), to give 1.8 g of N$^1$-(tetrahydropyranyl)biotin methyl ester m.p. 120°-122°, 45% yield mass ion (M$^+$=342), NMR δ ((CD$_3$)$_2$S=O, Bruker WH 400 MH$_z$) 6.85(1H, s, H-3); 4.80(1H, dxd, H.1'); 4.48(1H, m, H-6a); 4.10(1H, m, H-3a); 3.87(1H, dxd, H-5'); 3.40(1H, dxd, H-5'); 3.61(3H, s, OCH$_3$); 3.15(1H, m, H-4); 3.10(1H, d, H-6); 2.83(1H, dxd, H-6); 2.33 (2H, t, 2x H-10); 1.9–1.3(12H, complex m, 2x H-7, 2x H-8, 2x H-9; 2x H.2'; 2x H-3', 2x H-4').

b) N$^1$-(tetrahydropyran-2-yl)biotinol

A solution of N$^1$-(tetrahydropyran-2-yl)biotin methyl ester (0.5 g) in dry distilled tetrahydrofuran (25 ml) was added dropwise to a suspension of lithium aluminium hydride (0.27 g) in tetrahydrofuran (25 ml) stirred at 0° C. under a nitrogen atmosphere. Stirring was continued for 30 minutes and then the excess lithium aluminium hydride was destroyed by careful addition of a mixture of water:tetrahydrofuran, 1:19 v/v (20 ml). Butan-1-ol (150 ml) was added followed by 1N hydrochloric acid until the mixture was slightly acidic (pH 5.0). The aqueous layer was discarded and the butanol solution washed twice with saturated sodium bicarbonate solution (150 ml) then twice with saturated brine solution (150 ml). Water (150 ml) was added to the butanol solution and the mixture evaporated under reduced pressure at 40° C. The residue was fractionated on a column of silica gel (50 g; Merck Art. 9385) using CH$_2$Cl$_2$:CH$_3$OH, 9:1 (v/v) as eluant. After evaporation of solvents from combined appropriate fractions (as indicated by thin layer chromatography analysis on silica gel) there was thus obtained N$^1$- (tetrahydropyran-2-yl)biotinol (0.33 g, 70% yield) as an oil. Mass ion (M$^+$=314).

c) Methoxy morpholino [N'-(tetrahydropyran-2-yl)-biotinolyl]-phosphine (D)

Chloro(methoxy)morpholinophosphine (0.13 g) was added over a period of 5 minutes to a solution of N'-(tetrahydropyran-2-yl) biotinol (0.2 g) and N,N-diisopropylethylamine (0.35 g) in dry dichloromethane (5 ml) stirred at 0° C. under a nitrogen atmosphere. The temperature of the reaction mixture was increased to 22° C. over a period of 1 hour then the mixture was evaporated. The residual oil was dissolved in dichloromethane and fractionated on a column of silica gel (50 g; Merck Art. 9385) using triethylamine:ethyl acetate (7:3 v/v) as eluant. After evaporation of solvents from combined appropriate fractions there was thus obtained methoxy morpholino [N$^1$-(tetrahydropyran-2-yl)biotinolyl]phosphine (D) (50 mg, 17% yield). Mass ion (M+H)$^+$=462.

d) Hydroxy5'-(interferon-alpha$_2$-55)] N$^1$-tetrahydro pyran-2-yl biotinolyl phosphine oxide (B)

The fully-protected oligodeoxyribonucleotide sequence (c) known as sequence 55 in an interferon-alpha$_2$ gene synthesis described by M. D. Edge et al (Nucleic Acids Res., 1983, 11, 6419–6435 bound to a controlled pore glass support was prepared on an Appied Biosystems 380A DNA synthesiser from 5'-dimethoxytrityl-N$^2$-isobutyryl-2'-dexoyguanosine 0.2 μmol bound to controlled pore glass (Pore size 500A; Particle size 125–174 micron; loading 20–50 micromol/g from BDH limited) and 2-cyanoethyl-N,N-diisopropylamino phosphoramidites of 5'-dimethyoxytrityl-N$^6$-benzoyl-2'-deoxyadenosine, 5'-dimethoxytrityl-N$^4$-benzoyl-2'-deoxycytidine, 5'-dimethoxytrityl- N$^2$-isobutyryl-2'-deoxyguanosine and 5'-dimethoxytritylthymidine (BDH Chemicals Ltd). [Alternatively, the fully-protected oligodeoxyribonucleotide sequence may be prepared by the manual methods as described by Atkinson and Smith In 'Oligonucleotide Synthesis, a Pcactical Approach' (M J Gait Editor, IRL Press, Oxford, Washington, D.C. pp 35–81)]. A solution of methoxy morpholino [N$^1$-(tetrahydropyran-2-yl)biotinolyl]phosphine (D), 12.6 mg in 1,2-dichloroethane:acetonitrile (2:3 v/v) (0.6 ml) was used in place of a conventional nucleoside phosphoramidite in a modified coupling reaction on an Applied Biosystems 380A DNA synthesiser and added to the 5'-end of the fully protected oligodeoxyribonucleotide sequence interferon-alpha$_2$-55(C) to give a [5'-(interferon-alpha$_2$-55)] methoxy N$^1$-(tetrahydropyran-2-yl)biotinolyl phosphine (E) wherein the oligodeoxyribonucleotide sequence is fully protected as described above. The modified coupling reaction comprised the following:

(1) removal of the 5'-dimethoxytrityl group from the fully protected sequence with 3% trichloroacetic acid in 1,2-dichloromethane and (2) double coupling for 20 seconds and 5 seconds of the above mentioned phosphine (D) to the oligonucleotide sequence of (1) above. There then followed iodine oxidation of the so obtained fully protected [5'-(interferon-alpha$_2$-55)]methoxy N$^1$-(tetrahydropyran-2-yl)biotinolyl phosphine (E) to give the corresponding phosphate (F). This phosphate derivative was then partially deprotected to remove all phosphate protecting groups and the oligonucelotide sequence cleaved from the controlled pore glass support. Both operations were performed automatically on the DNA synthesiser using an appropriate ammount of thiophenolate ion and then ammonium hydroxide (sp. gr. 0.91). The resulting ammonium hydroxide solution was then heated at 55° C. for 6 hours, then evaporated and the residue containing hydroxy [5'-(interferon-alpha$_2$-55] N$^1$-(tetrahydropyran-2-yl) biotinolyl phosphine oxide (B) dissolved in ethanol/water (3:7 v/v. 1.5 ml). This solution was then used directly in the subsequent deprotection stage.

Example 2

Biotinolyl hydroxy [5'-(interferon-alpha$_2$-55)]phosphine oxide (A)

$N^1$-(4,4'-dimethoxytrityl)biotinolyl hydroxy [5'-(interferon-alpha$_2$-55]phosphine oxide (G) 0.1 μmol obtained as described below was treated with 2 ml of 80% acetic acid containing 4 drops of pyridine at room temperature for 20 minutes. Acetic acid was removed by evaporation at reduced pressure and then azeotroping with water (2 ml) and n-butanol (0.5 ml). The title oligonucleotide (A) was taken up in 1.5 ml of 15% ethanol, H$_2$O and purified by a two stage High Pressure Liquid Chromatography (HPLC) procedure as outlined in Example 1.

The first HPLC on Partisil 10-SAX (60% formamide, 0–100% in 50', linear gradient) gave the title biotinylated oligonucleotide (A) as the most retained peak with a retention time of 17 minutes as compared to 16 minutes for the parent oligonucleotide (C). The second HPLC on μ-Bondapak C-18 gave retention times of 31.0 and 28.8 minutes respectively. When repeated with μ-Bondapak (10–100% in 40') retention times of 29.3 and 14.4 minutes respectively were recorded.

The protected biotinylated oligonucleotide (G) used as starting material was prepared as follows:

a) $N^1$-(4,4'-Dimethoxytrityl)biotin methyl ester.

A solution of anhydrous D(+)biotin methyl ester (5.0 g; dried by azeotropic distillation with anhydrous pyridine) and 4,4'-dimethoxytrityl chloride (7.25 g) in anhydrous pyridine (125 ml) was stirred at 22° C. for 1 hour. Methanol (20 ml) was added and the mixture evaporated. The residue was dissolved in methylene chloride (300 ml) and washed successively with saturated sodium bicarbonate solution (2×200 ml) and saturated brine solution (2×200 ml) then dried over anhydrous magnesium sulphate and evaporated. The residual oil was dissolved in methylene chloride (80 ml) and purified on a Waters Prep 500 HPLC 2 cartridge system (Waters Associates, Inc.) using a gradient of 0 to 8% methanol in methylene chloride (81.) After evaporation of appropriate fractions (300 ml; 14 to 16) there was thus obtained $N^1$-(4,4'-dimethoxytrityl)biotin methyl ester as a golden yellow solid. Mass ion (M+ =560, NMR δ(CDCl$_3$, 200 MH$_z$) 7.22(9H, m, aromatic protons); 6.83(4H, d, aromatic protons); 4.94(1H, broad s, NH); 4.35(2H, m, H$_{3a}$,H$_{6a}$); 3.78(3H, s, methoxy protons); 3.68(3H, s, methyl ester protons); 3.11(1H, m, H$_4$); 2.47(1H, dxd, J gem=13 H$_z$, J$_{16,6a}$=1.7 H$_z$,H$_6$); 2.29(2H, t, J$_{9,10}$6.7 H$_z$, 2x H$_{10}$); 2.27(1H, dxd, J gem=13 H$_z$ J$_{6,6a}$=5.3 H$_z$,H$_6$); 1.5(6H, complex multiplet, 2x H$_8$, 2xH, 2 xH$_9$). (4.4 g; yield 40%).

b) $N^1$-(4,4'-dimethoxytrityl)biotinol

A solution of $N^1$-(4,4'-dimethoxytrityl)biotin methyl ester (4.0 g) in dry distilled tetrahydrofuran (300 ml) was added dropwise to a suspension of lithium aluminium hydride (1.3 g) in tetrahydrofuran (130 ml) at 22° C. Stirring was continued for 20 minutes, then the excess lithium aluminium hydride was destroyed by careful addition of a mixture of water:tetrahydrofuran (1.19 v/v; 100 ml). Butan-1-ol (500 ml) was added and the mixture washed successively with saturated sodium sulphate solution (100 ml) and water (100 ml) then evaporated under reduced pressure at 40° C. The residual brown oil was dissolved in methylene chloride (80 ml) and fractionated on a Waters Prep 500 HPLC 1 cartridge system using methanol:methylene chloride (1.9 v/v) as eluant. After evaporation of appropriate fractions (150 ml; 5 to 8) there was thus obtained $N^1$-(4,4''dimethoxytrityl)biotinol as a brown oil. Mass ion (M+ =532), (3.02 g; 80% yield).

c) [$N^1$-(4,4'-dimethoxytrityl)biotinolyl]methoxy morpholino phosphine (H)

In a similar manner to that employed in Example 1, part (c) but using $N^1$-(4,4'-dimethoxytrityl)biotinol instead of $N^1$-(tetrahydropyran-2-yl)biotinol there was obtained [$N^1$-(4,4'-dimethoxytrityl)biotinolyl]methoxy morpholino phosphine (H) as a colourless oil in 44% yield with the following NMR data: (CDCl$_3$, 200 MH$_z$) 7.22(9H, m, aromatic protons); 6.80(4H, d, aromatic protons), 4.92(1H, s, NH); 4.33(2H, m, H$_{3a}$,H$_{6a}$); 3.8(3H, s, methoxy protons); 3.68(1H, m, H$_4$); 3.6(2H, t, J$_{10,11}$=4.2 H$_z$ 2x H$_{11}$); 3.45(3H, d, J$_P$,OCH$_3$=11.7 H$_z$, P OCH$_3$); 3.12(4H, m, morpholino protons); 2.47(1H, dxd, J gem=13.3 H$_z$, J$_{6,6a}$=15 H$_z$,H$_6$); 2.26(1H, dxd, J gem=11.7 H$_z$, J$_{6,6a}$=5.0 H$_z$,H$_6$), 1.52(8H, complex multiplet, 2x H$_7$, 2x H$_8$, 2x H$_9$, 2 xH$_{10}$).

d) [$N^1$-(4,4'-dimethoxytrityl)biotinolyl]hydroxy [5'-(interferon-alpha$_2$-55]phosphine oxide (G).

The fully protected interferon-alpha$_2$-55 sequence (C) bound to a controlled pore glass support was prepared as described in example 1, part (d). [$N^1$-(4,4'-dimethoxytrityl)biotinolyl]-methoxy morpholino phosphine (H) as obtained in (c) above was used in place of a conventional nucleotide in a modified coupling reaction on an Applied Biosystems 380A DNA synthesiser and added to the 5' end of the above mentioned oligo-deoxyribonucleotide sequence interferon-alpha$_2$-55 to give an $N^1$-(4,4'-dimethoxytrityl)biotinolyl [5'-(interferon-alpha$_2$-55)]methoxy phosphine (J) wherein the oligodeoxyribonucleotide sequence is fully protected as described above.

The modified coupling reaction comprised the following: [$N^1$-(4,4'-dimethoxytrityl)biotinolyl]methoxy morpholino phospine (H) (100 mg) was azeotroped three times with anhydrous CH$_3$CN and then dissolved in 1,2-dichloroethane (333 μl); CH$_3$CN (222 μl).

An Applied Biosystems Synthesiser small scale synthesis programme abibc 103 with a 3×100 secs coupling step (normal procedure 1×30 secs) with no capping step and followed by iodine oxidation of the phosphite group to give a phosphate (K). The phosphate protecting groups were removed and the oligonucleotide was cleaved on the synthesiser from the support using ammonium hydroxide (sp.gr. 0.91) and the base protecting groups were then removed by treatment with 0.910 sp.gr. ammonia (50° C. and 4–5 hrs.) to give the title phosphine oxide (G) which was used directly in the next step.

Example 3

Biotinolyl hydroxy [5'-(interferon-alpha$_2$-55)]phosphine oxide (A)

Hydroxy [5'-(interferon-alpha$_2$-55] $N^1$-(6-methoxytetrahydropyran-2-yl)biotinolyl phosphine oxide (L)], obtained as described below, was treated with hydrochloric acid (0.1N, 600 μl) and the mixture allowd to stand for 45 minutes at 22° C. Ammonium hydroxide (sp. gr. 0.91, 126 μl) was added and the title biotinylated oligonucleotide (A) was then purified by a High Pressure Liquid Chromatography (HPLC) procedure as outlined in Example 1.

The first HPLC on Partisil 10-SAX (60% formamide, 0–100% in 50', linear gradient) gave the title biotinylated oligonucleotide (A) as the most retained peak with a retention time of 22.2 minutes as compared to 21.5 minutes for the parent oligonucleotide (C). The second HPLC on μ-Bondapak C-18 (10–45% in 40') gave retention times of 17.5 and 16.0 minutes respectively.

The protected biotinylated oligonucleotide used as starting material was prepared as follows:

a) $N^1$-(6-methoxytetrahydropyran-2-yl)biotin methyl ester.

The procedure described in Example 1, part (a) was repeated with 2,3-dihydro-2-methoxy-4H-pyran replacing 2,3-dihydro-4H-pyran. The crude product was purified by flash silica gel chromatography (Merck Kieselgel 60, Art 9385) using methylene chloride:methanol (94:6 v/v) as eluant. After removal of solvents from appropriate fractions the title compound was thus obtained in 22% yield with the following NMR data:

δ (CDCl$_3$, 200 MH$_z$) 5.78 and 5.63(1H, 2s, NH proton), 5.46(1H, dxd, methoxy THP proton); 4.77 (1H, br.d, methoxy THP proton); 4.48(1H, complex multiplet, H$_{3a}$); 4.22(1H, complex multiplet, H$_{6a}$); 3.68(3H, s, methyl ester protons); 3.68(3H, d, methoxy THP protons): 3.44(3H, d; methoxy THP protons); 3.18(1H, complex multiplet H$_4$); 2.86(2H, complex multiplet, 2 xH$_6$); 2.32 (2H, t, 2 xH$_{10}$); 1.58(12H, m, methoxy THP protons and 2 xH$_7$, 2 xH$_8$ and 2 xH$_9$).

b) $N^1$-(6-methoxytetrahydropyran-2-yl)biotinol.

The procedure described in Example 1, part (b) was repeated with $N^1$-(6-methoxytetrahydropyran-2-yl)biotin methyl ester replacing $N^1$-(tetrahydropyran-2-yl)biotin methyl ester to give the title compound in 42% yield. Mass ion $(M+H)^+ = 345$.

c) Methoxy $N^1$-(6-methoxytetrahydropyran-2-yl)biotinolyl]-morpholino phosphine (M)

The procedure described in Example 1, part (c) was repeated with $N^1$-(6-methoxytetrahydropyran-2yl)biotinol and replacing $N^1$-(tetrahydropyran-2-yl)biotinol and triethylamine:ethyl acetate (4:1, v/v/) replacing triethylamine:ethyl acetate (7:3, v/v) as eluant to give the title compound (M) in 20% yield. Mass ion $(M+H)^+$ 492.

d) Hydroxy [5-(interferon-alpha$_2$-55)] $N^1$-(6 methoxytetrhydropyran-2-yl)biotinolyl phosphine oxide (L)

The fully protected interferon-alpha$_2$-55 sequence bound to a controlled pore glass support was prepared as described in above was used in place of a conventional nucleotide phosphoramidite in a modified coupling reaction on an Applied Biosystems 380A DNA synthesiser and added to the 5'-end of the oligodeoxyribonucleotide sequence interferon-alpha$_2$-55 (C) to give a [5'-(interferon-alpha$_2$-55)]methoxy $N^1$-(6-methoxytetrahydropyran-2-yl)biotinolyl phosphine (N) wherein the oligodeoxyribonucleotide sequence is fully protected as described above. The modified coupling reaction comprised the following:

Methoxy [$N^1$-(6-methoxytetrahydropyran-2-yl)biotinolyl]morpholino phosphine (M) (78 mg) was azeotroped three times with anhydrous CH$_3$CN and then dissolved in 1,2-dichloroethane (360 μl); CH$_3$CN (240 μl).

An Applied Biosystems Synthesiser small scale synthesis programme abibc 103 with a 3×100 secs. coupling step (normal procedure 1×30 secs) with no capping step and followed by iodine oxidation of the phosphite group to phosphate (P). The phospate protecting groups were removed and the oligonucleotide was cleaved from the support on the synthesiser using ammonium hyroxide (sp.gr. 0.91) and the base protecting groups were then removed by treatment with 0.910 s gr. ammonia (50° C. and 4–5 hrs.) top. give the title phosphine oxide (L) which was then taken up ine 1.5 ml of 15% EtOH,H$_2$O to be used directly in the next step.

The avidin-agarose binding of biotinylated oligonucleotides of the present invention is illustrated by the following: Biotinylated oligonucleotides in 0.5 ml of buffer (PBS, 0.1% Tween 20) were added to a column (0.2 ml) of avidin-agarose (Sigma Chemical Company Ltd) containing 7.4 units of a avidin. The column was washed with PBS, 0.1% Tween and fractions (0.5 ml) were collected. The parent oligonucleotide sequence interferon alpha$_2$-55 (C) passed through the column unretarded.

a) A solution of biotinylated oligonucleotide (A), as prepared in example 2, (0.43 OD$_{260}$ units) in buffer was applied to the avidin-agarose column. A total of 0.06 OD$_{260}$ units was recovered from the column. The percentage of (A) retained was thus 86%.

b) A solution of (A), as prepared in example 3, (0.25 OD$_{260}$ units in buffer was applied to the avidin-agarose column. A total of 0.041 OD$_{260}$ units was recovered from the column. The percentage of (A) retained by the column was thus 84%.

c) A solution of the protected biotinylated oligonucleotide (L), (0.294 OD$_{260}$ units) in buffer was applied to the column. A total of 0.222 OD$_{260}$ units was recovered from the column. The percentage of (L) retained was thus 24%.

d) A solution of (A), as prepared in example 1, (0.42 OD$_{260}$ units in buffer (0.5 ml) was applied to the avidin-agarose column (0.55 ml; 21 units of avidin as described above. A total of 0.076 OD$_{260}$ units was recovered from the column. The percentage of (A) retained was thus 82%.

Hybridisation Example

Serial dilutions of plasmids 1205 (containing the α$_2$ interferon gene sequence) and F6 (containing the gene sequence of the F6 α$_2$ interferon analogue) (see, for example European Patent application, publication No. 202758) were spotted onto nitrocellulose Shleicher & Schuell, BA 85 SB) using a Schleicher Schuell Minifold II (first spot 1 μg, thereafter 3-fold dilutions). Prior to spotting each plasmid dilution was alkaline denatured at 100° C. for 10 mins in 300 μls 0.2M NaOH, 7x SSC, 56 mM Tris HCl pH 7.4, then chilled in an ice bath and neutralised by the addition of 70 μl 1M Tris HCl pH 7.0. The DNA was immobilised by baking the nitrocellulose at 80° C. for 2 hrs under vacuum.

Filters were prehybridised for 1 hr at 65° C. in 5× Denhardts, 5x 55C, 50 mM sodium phosphate pH 7.0, 1% glycine, 0.1% SDS, 100 μg.ml sonicated and boiled herring sperm DNA. Hybridisation was overnight at room temperature in 5x SSC, 0.5% Nonidet P40 (BDH 56009), 250 μg/ml tRNA (Sigma Type X-5, R0128), with the oligonucleotide present in 50 fold molar excess. The prehybridisation and hybridisation were carried out in a sealed plastic bag.

Following overnight hybridisation the filters were washed twice (each wash lasting 5 minutes) at room temperature in 6x SSC, 0.6% sodium pyrophosphate, 20mM sodium phosphate pH7 and then once in the same buffer at 40° C. for 3 mins. Spots of hybridised probe were visualised using the BRL DNA detection kit (cat. #82395A). Briefly the filters underwent the following incubations:

1. Room temperature, 1 minute in 0.1M Tris.HCl pH7.5, 0.1M NaCl, 2 mM MgCl₂, 0.05% (v/v) Triton X 100 (Buffer 1)
2. 37° C., 20 minutes in 3% (v/v) BSA in Buffer 1 (Buffer 2)
3. Room temperature, 10 minutes in Buffer 1 containing 2 μg.ml streptavidin (approximately 3 ml solution/100 cm² nitrocellulose).
4. Room temperature wash for 3 minutes in Buffer 1
5. As 4.
6. As 5.
7. Room temperature, 10 minutes in Buffer 1 containing 1 μg/ml biotinylated alkaline phosphatase (approximately 3 ml solution/100 cm² nitrocellulose)
8. Room temperature wash for 3 minutes in Buffer 1
9. As 8
10. Room temperature wash for 3 minutes in 0.1M Tris. HCl (pH9.5), 0.1M NaCl, 50 mM MgCl₂ (Buffer 3).
11. As 10.
12. Room temperature, with alkaline phosphatase substrate solution (NBT/BCIP in Buffer 3) (e.g. as described by Leary et al, Proc. Natl. Acad. Sci. USA. (1983), 80, 4046).

Incubations 1–11 were carried out in sandwich boxes. Substrate incubation 12 was performed in a sealed plastic bag in the dark. Colour was allowed to develop for ½ hr, after which time the 37 ng 1205 spot was visible on the filter. Fewer F6 spots were visible due to the destabilisation of the hybrid caused by the mismatches in this analogue.

Formulae referred to in the Examples

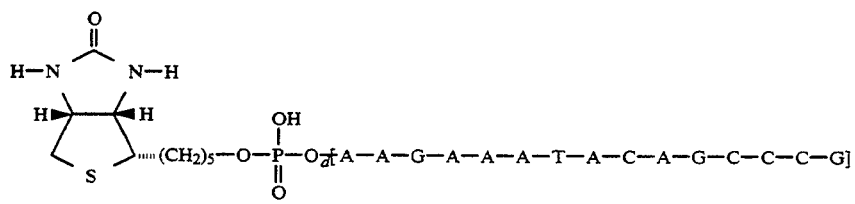
(A)

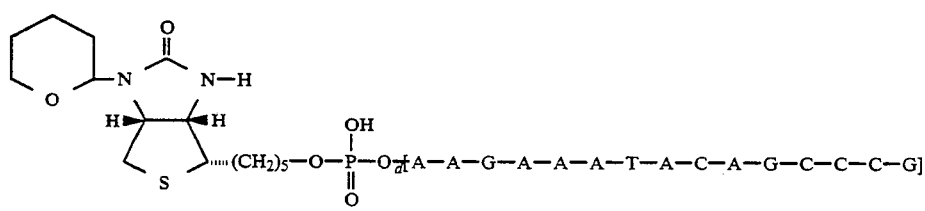
(B)

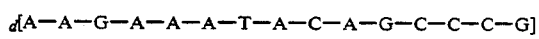
(C)

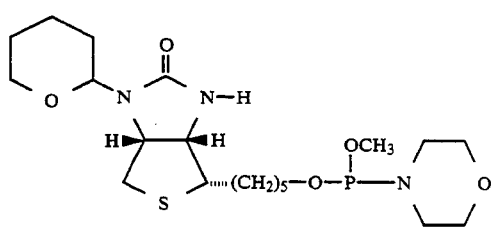
(D)

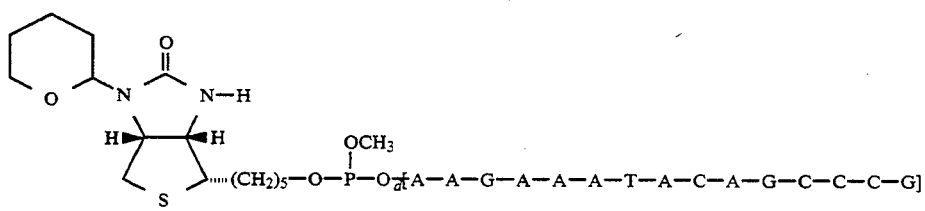
(E)

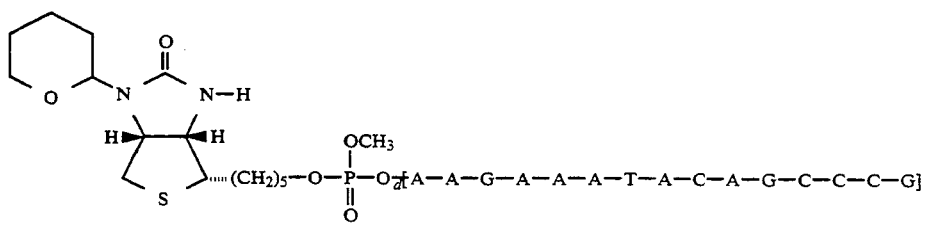
(F)

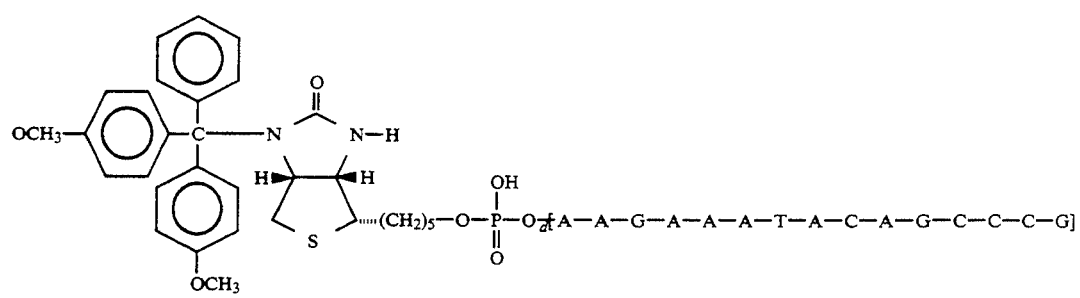
(G)
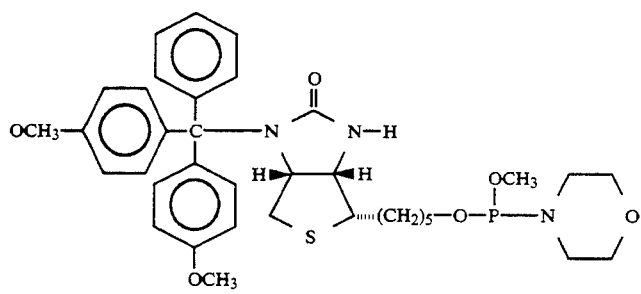
(H)
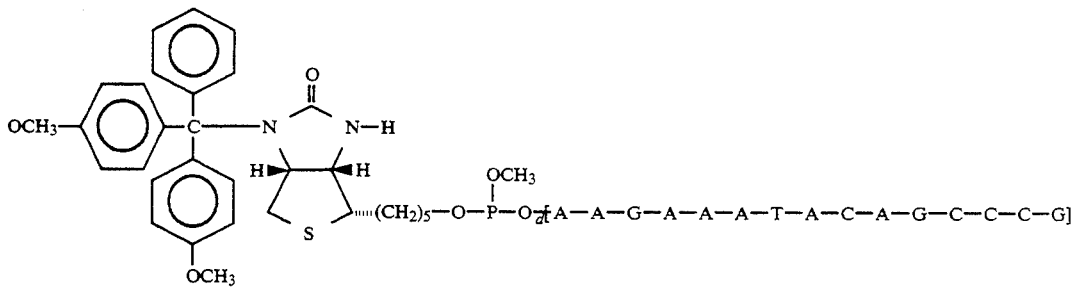
(J)
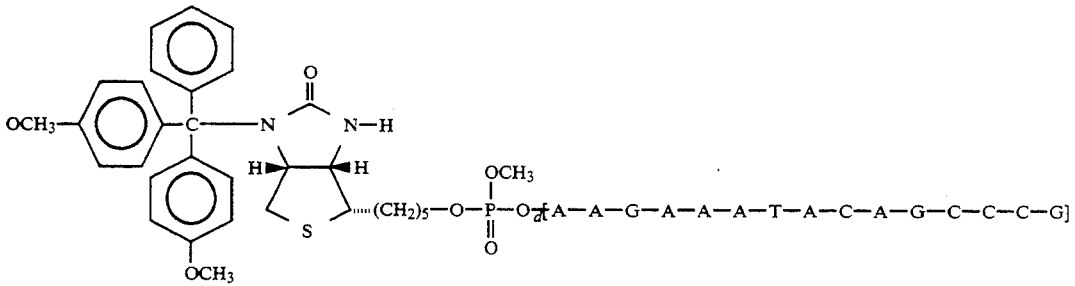
(K)
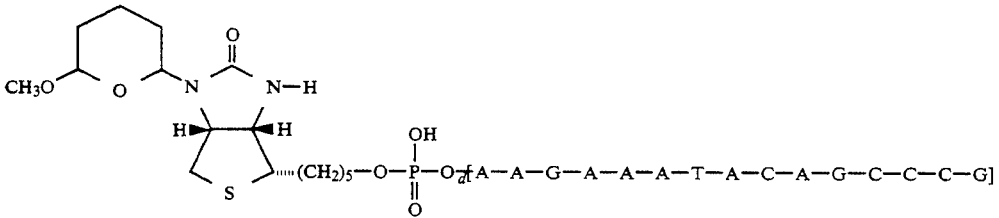
(L)
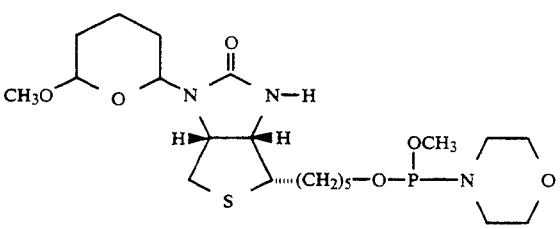
(M)

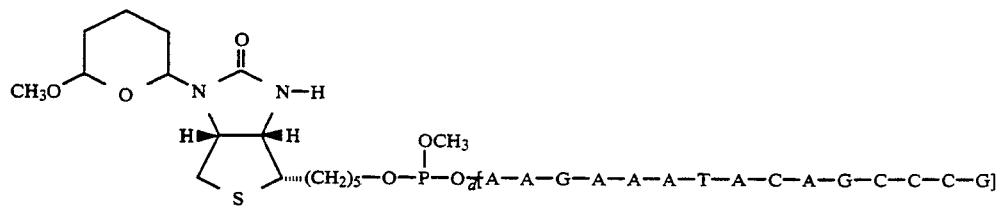
(N)
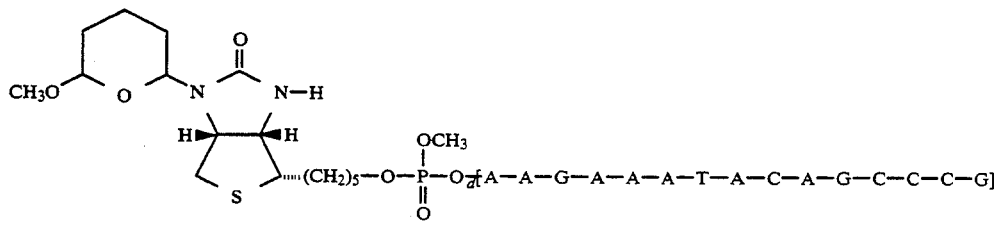
(P)
Formulae
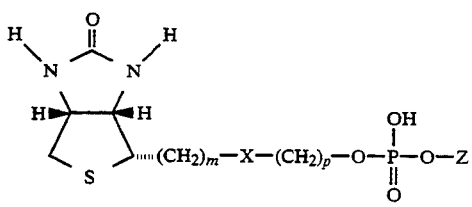
(I)
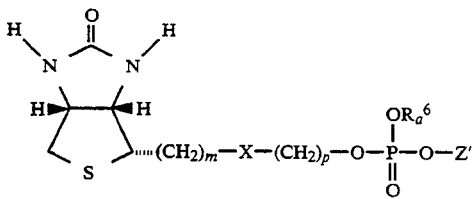
(Ia)
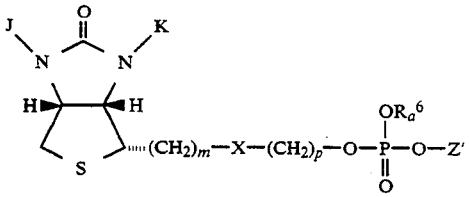
(II)
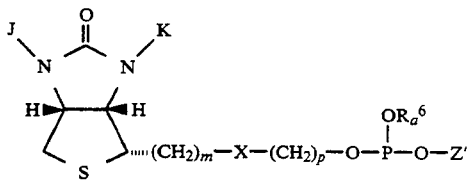
(III)
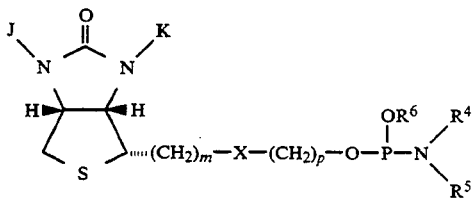
(IV)
(V)

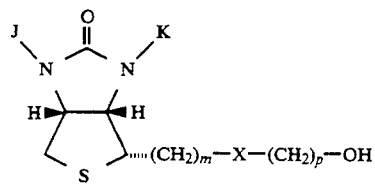
(VI)
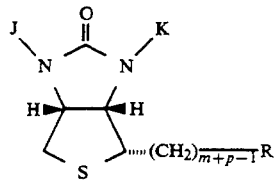
(VII)
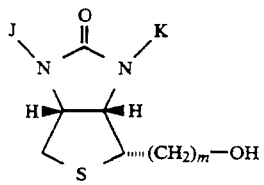
(VIII)
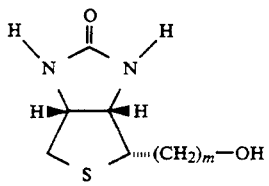
(XV)
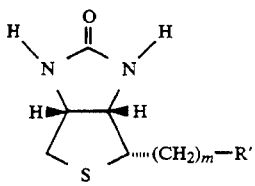
(XVI)
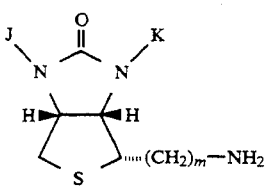
(XVII)
(XVIII)
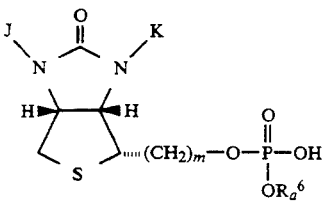
(XIX)
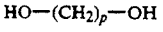
(IX)
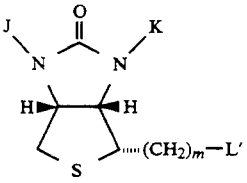
(X)

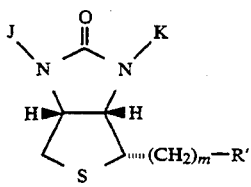

(XI)

(XII)

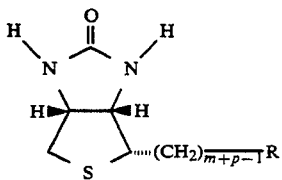

(XIII)

(XIV)

We claim:

1. A compound of formula IV

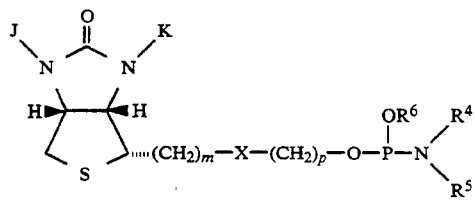

wherein m is 4 or 5, X represents a direct bond, —O—P-(O)(OR$^6{}_a$)—O—, —S—, —O—, —CONH—, —NH-CONH— or N—R$^8$ wherein R$^8$ represents a straight chain or branched C$_{1-10}$ alkyl group, p is an integer from 0 to 16 with the proviso that where X is other than a direct link, p is an integer of at least 2, R$^6{}_a$ represents a hydrogen atom or a phosphate protecting group; and J and K, which may be the same or different, each represents a hydrogen atom or a protecting group compatible with nucleotide phosphorylation which group increases the lipophilicity of the compound, at least one of J and K being other than hydrogen, or an isoequivalent thereof, R$^4$ and R$^5$, which may be the same or different, each represent a 1–10C straight chain or branched alkyl group or R$^4$ and R$^5$ together with the nitrogen atom therebetween represent a saturated 5 or 6 membered heterocyclic ring or a morpholino group, and R$^6$ is a phosphate protecting group, or isoequivalent thereof.

2. The compound according to claim 1 wherein X is a direct bond or a —O—P(O)(OR$^6$)—O— group, in which latter case P is at least 2.

3. The compound according to claim 1 wherein X(CH$_2$)$_p$— is —CONH(CH$_2$)$_4$—, —NHCONH(CH$_2$)$_4$— or —O—P(O)(OR$^6$)—O—(CH$_2$)$_8$.

4. The compound according to claim 1 wherein m=5.

5. The compound according to claim 1 wherein R$^6$ is methyl or 2-cyanoethyl.

6. The compound according to claim 1 wherein R$^4$ and R$^5$ are each independently methyl or isopropyl.

7. The compound according to claim 1 wherein —NR$^4$R$^5$— is a 5 or 6 membered saturated ring or morpholino group.

8. The compound according to claim 1 wherein —NR$^4$R$^5$ is N-piperidino or N-morpholino.

* * * * *